United States Patent [19]

Chen

[11] 4,223,150
[45] Sep. 16, 1980

[54] PROCESS FOR PREPARING 1,1'-DIALKYL-4,4'-BIPYRIDYLIUM DIHALIDE

[75] Inventor: Ming F. Chen, Taichung, Taiwan

[73] Assignee: Cheng Hong Chemical Co., Ltd., Taichung, Taiwan

[21] Appl. No.: 949,529

[22] Filed: Oct. 10, 1978

[51] Int. Cl.$^2$ .................................... C07D 213/22
[52] U.S. Cl. ............................................ 546/258
[58] Field of Search .................. 260/296 D; 546/258

[56] References Cited

U.S. PATENT DOCUMENTS 3,530,141  9/1970  Downes et al. .................. 546/258

Primary Examiner—Alan L. Rotman

[57] ABSTRACT

1,1' dialkyl -4,4'-bipyridylium dihalide is prepared by heating 4,4'-bipyridyl with an α-halogen substituted organic acid of formula X R$_1$COOH where X is Cl or Br, R is C$_{1-3}$, preferably monochloroacetic acid alkyl group in the presence of water until the pH is below 4.0.

3 Claims, No Drawings

PROCESS FOR PREPARING 1,1'-DIALKYL-4,4'-BIPYRIDYLIUM DIHALIDE

This invention relates to a process for preparation of alkyl quaternary salts of 4,4'-bipyridyls which are useful as active ingredients for herbicides, and particularly to a process for preparing 1,1'-dialkyl -4,4'-bipyridylium dihalide.

Methods for the production of N-alkyl -4,4'-bipyridylium diquaternary salts by using alkyl halides or alkyl sulphates as quaternising agents have been proposed and employed extensively by industry. These quaternising agents, however, suffer from various disadvantages. For example, dimethylsulphate is a toxic substance which is dangerous to handle, while methyl chloride requires the use of pressures above atmospheric pressure to obtain a satisfactory yield of product.

To overcome the difficulties of these methods an alternative reaction process has been proposed by Imperial Chemical Industries Limited in U.K. Pat. No. 1,135,682. This process is characterized by heating 4,4'-bipyridyls such as 2,2'-dimethyl-4,4'-bipyridyl and 2,6-dimethyl -4,4'-bipyridyl with an aliphatic carboxylic acid having 2 to 5 carbon atoms and halogen substituent in the alpha ($\alpha$) position, in the absence or presence of an organic inert diluent. However, the reaction product of this process is either a solid or a liquid containing large amount of solid, so that purification steps, for example distillation or recrystallization are needed. Moreover, the yield is about 75% and even in the most preferable example, the same shows on the order of 90%, which means the reaction product still contains considerable amount of unreacted materials and/or reaction intermediates which have to be removed before the product is usable for formulation.

The purification equipment causes extra expense and eventually increased manufacturing cost. Furthermore, the process provides no measure to confirm the reaction end-point, this making it difficult to raise conversion (yield) to a desired level.

There is therefore a need for an inexpensive, improved process which can eliminate the drawbacks of the prior art process including U.K. Pat. No. 1,135,628.

There is also a need for a process for preparing 1,1'-dialkyl 4,4'-bipyridylium dihalide without the use of alkyl halides or alkyl sulphates. There is also a need for a process for preparing 1,1'-dialkyl- 4,4'-bipyridylium dihalide without using organic diluents and without purifying the reaction product to obtain a high yield of the product for direct use in formulation. There is also a need for a process for preparing 1,1'-dialkyl-4,4'-bipyridylium dihalide where the reaction end-point can readily be controlled and the desired yield of the product be obtained.

According to the present invention there is provided a process for the preparation of 1,1'-dialkyl -4,4'-bipyridilium dihalide in which 4,4'-bipyridyl is reacted with a $\alpha$-halogen substituted organic acid of a general formula

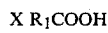

wherein X is Cl or Br in $\alpha$-position, $R_1$ is a $C_1$-$C_3$ alkylene group, under heating in the presence of water and terminating the reaction at the pH value of below 4.0.

Theoretically speaking, the 4,4'-bipyridyl has a reactive nitrogen atom and this nitrogen atom will form an acid salt upon contact with either strong or weak acids. The COOH group of the acid salts thus formed is chemically more active and decomposable than the COOH group of the simple $XR_1COOH$.

In view of the decomposition theory, it might be assumed that $XR_1CO$— radical will further combine with 4,4'-bipyridyl to form 1,1'-diacyl -4,4'-bipyridylium dihalide. But when heating at 100° C., they will react vigorously and boil to generate gas. This gas is assumed to be $CO_2$ from the chemical formula $XR_1COOH$. In order to ascertain this, the following experiments were conducted:

(1) Upon introducing the said gas into the clear upper layer of slaked lime milk, the layer was immediately whitened. From this fact, it is qualitively identified that the gas was $CO_2$ or a gas containing large amount of $CO_2$.

(2) In case that $XR_1COOH$ is gradually added to the aqueous solution of 4,4'-bipyridyl, the solution, at the time of salt formation should be in strong acidity and will change to neutrality or near neutrality after the generation of $CO_2$. This phenomenon is assumed to be that the salt formation from the reaction of 4,4'-bipyridyl with $\alpha$-halogen substituted organic acid leads the reaction mixture exhibits strong acidity in the early stage of the reaction as shown by low pH value, thereafter the so formed acid salt decomposes by heating and generates $CO_2$ to form nonacidic substances, that causes pH to change to neutrality or near neutrality. From the fact that precipitate was formed immediately when admixing reaction product with the anionic dispersant, it can be ascertained that the reaction product should be some kind of ionized compounds. The reaction scheme may be shown as follows.

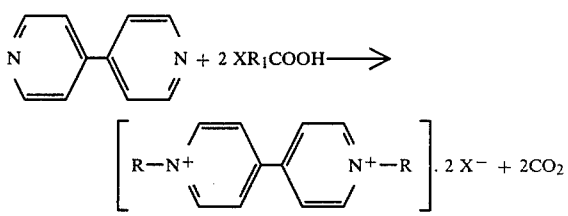

wherein X represents a halogen atom, R represents an alkyl group, $R_1$ represents a substituted alkyl group.

(3) In order to further confirm the aforementioned reactions of items (1) and (2), the following experiment was conducted.

To the hot solution of 4,4'-bipyridyl was added $\alpha$-halogen substituted organic acid such as mono-chloroacetic acid while heating the mixture at the temperature of 120°–130° C. The $CO_2$ generated during the reaction was totally introduced into 20% potassium hydroxide solution. After completion of the reaction, there was analysed the potassium carbonate formed from the interaction of $CO_2$ and potassium hydroxide and calculated the amount of $CO_2$ being adsorbed and monochloroacetic acid being consumed. In the meantime, there was analysed the content of 1,1'-dimethyl -4,4-bipyridylium dichloride by using spectrophotometer and calculate back the amount of monochloroacetic acid. The results showed that (a) the monochloroacetic acid actually used, (b) the monochloroacetic acid calculated from the analytic data of the final reaction product and, (c) The monochloroacetic acid calculated from after the generated $CO_2$ has been absorbed by the potassium hydroxide are almost completely in conformity with one another.

From the above experiments, it has been confirmed that the final reaction product in accordance with the present invention is totally the desired product and that the conversion of 4,4'-bipyridyl was almost 100%.

The invention is illustrated by the following Examples. The spectrophotometer used throughout the Examples was of the Type UV-200 which is made and sold by Shimazu CO., Japan and the analysis was carried out according to the method described in the publication "CIPAC".

EXAMPLE 1

A three-necked flask of 500 ml equipped with a countercurrent cooler, a thermometer and a separating funnel was charged with 50.5 g of 4,4'-bipyridyl and 30.0 g of water, and then placed on a heating-type magnetic stirrer. During agitation, the contents (reaction mixture) were maintained at 120° C. and saturated aqueous solution of mono-chloroacetic acid was added dropwisely from the separating funnel. During addition the content boiled vigorously and generated gas, which was introduced into 20% potassium hydroxide aqueous solution for absorption by said solution. In the initial stage the pH value of the reaction mixture was 8.0-9.0 but at the end of addition of the mono-chloroacetic acid the pH dropped to 2.0. The reaction mixture was further heated at 120° C. for 10-15 minutes and completed the reaction when pH reached 2.5-3.0. 127 g of reaction product in liquid form was obtained, which was analysed by the method described in "CIPAC". The content of 1,1'-dimethyl-4,4'-bipyridylium dichloride salt was 54.99 g. The conversion based on the starting material 4,4'-bipyridyl was 99.0%. This reaction product was kept at 0° C. and the crystalline substances separated by paper chromatography. The result showed that the substance was completely in conformity with the standard sample of 1,1'-dimethyl-4,4'-bipyridylium dichloride. The content of reaction intermediate, i.e. 1-methyl-4,(4'-pyridyl) pyridylium monochloride showed 0.45% by liquid chromatography.

The potassium carbonate produced from the $CO_2$ and 20% potassium hydroxide solution was 28.0 g. The conversion calculated back from this was 98.9%, which is almost in consistency with the value, i.e. 99.0% calculated from CIPAC method.

EXAMPLE 2

Example 1 was repeated except that the reaction was carried out at the temperatures of 40° C., 50° C., 60° C., 70° C., 80° C., 90° C., 100° C., 110° C., and 120° C. with the reaction time as listed in the following table.

The results are also shown in the same table.

| Reaction Temp. (C.) | Reaction Time & Conversion | | |
|---|---|---|---|
| | 60 min | 90 min | 120 min |
| 40 | 0% | 0% | 0% |
| 50 | 2.5 | 2.6 | 3.0 |
| 60 | 18.0 | 20.1 | 21.5 |
| 70 | 32.8 | 35.5 | 40.2 |
| 80 | 43.6 | 48.1 | 51.5 |
| 90 | 62.1 | 62.2 | 70.6 |
| 100 | 80.3 | 85.2 | 88.7 |
| 110 | 92.3 | 98.2 | 95.6 |
| 120 | 98.0 | 99.0 | 99.0 |

EXAMPLE 3

Example 1 was repeated except that 0.2, 0.3, 0.4, 0.5, 1.0, 2.0, 3.0, 4.0, and 5.0, times of water based on the 4,4'-bipyidyl were used and that the reactions were carried out at the varied temperatures as shown in the following table. Also in the table the conversions of 4,4'-bipyridyl in each reaction were shown.

| Water used | | Reaction Time (min) | Reaction Temp. (C.) | Phase of reactant | Conversion (%) |
|---|---|---|---|---|---|
| No. of times | g | | | | |
| 0.2 | 10.10 | 120 | 120 | Solid | 90.1 |
| 0.3 | 15.15 | " | " | Semisolid | 93.3 |
| 0.4 | 20.20 | " | " | liquid cont. solid | 96.5 |
| 0.5 | 25.25 | " | " | liquid | 99.0 |
| 1.0 | 50.50 | " | 110 | " | 99.1 |
| 2.0 | 101.00 | " | 105 | " | 99.1 |
| 3.0 | 151.50 | " | " | " | 99.2 |
| 4.0 | 202.00 | " | " | " | 99.2 |
| 5.0 | 252.50 | " | 103 | " | 99.2 |

EXAMPLE 4

Example 1 was repeated except that the reactions were terminated at the time when pH reached 6.0, 5.0, 4.0, 3.0, 2.5, 2.0. After reactions were completed the conversion was determined and the percentage of residual 1-methyl-4,(4'-bipyridyl) pyridylium monochloride (hereinafter refer to 1-methyl compound) by employing liquid chromatography. The results were shown in the following table:

| pH | Reaction Temp | Reaction Time | Conversion | 1-methyl Compound | Mono-Chloro acetic acid |
|---|---|---|---|---|---|
| 6.0 | 120° C. | 120 min | 85.1% | 13.5% | 55.6 g |
| 5.0 | " | " | 87.2 | 11.2 | 56.2 |
| 4.0 | " | " | 92.6 | 6.8 | 58.0 |
| 3.0 | " | " | 98.0 | 1.4 | 59.7 |
| 2.5 | " | " | 99.0 | 0.4 | 60.5 |
| 2.0 | " | " | 98.9 | 0.4 | 61.6 |

EXAMPLE 5

In Example 1 mono-chloroacetic acid was replaced by a halogen organic acid having a formula of $XR_1COOH$, wherein X and $R_1$ are as defined above, and the following products obtained:

| Halogen organic acid | Product |
|---|---|
| α-bromoacetic acid | 1,1'-dimethyl-4,4'-bipyridylium dibromide |
| α-chloro-N-propionic acid | 1,1'-dipropyl-4,4'-bipyridylium dichloride |
| α-bromo-N-propionic acid | 1,1'-dipropyl-4,4'-bipyridylium dibromide |

In each of these examples the conversions of 4,4'-bipyridyl were all in the range of from 95% to 98%, which are considerably higher than those of prior art. From the foregoing, it is apparent that the present invention is more advantageous compared with the conventional method of using methyl chloride or methyl sulphate as quaterning agents in that:

(a) The reaction time is considerably shorter;

(b) The conversion is higher, that is approximately 100%, while that in the conventional method it is in the order of 90%. These are considered to be attributable to the following reasons:

1. The reaction of 4,4'-bipyridyl and gaseous methyl chloride could not be effected smoothly except by maintaining the temperature at 120° C.–130° C. either under atmospheric pressure or above.

2. As from the reaction mechanism, one molecule of the methyl chloride initially reacts with one of the two nitrogen atoms in the 4,4'-bipyridyl to form 1-methyl -4,(4'-pyridyl) pyridylium monochloride and then reacts (combines) with the other nitrogen atom to form the desired compound 1,1'-dimethyl -4,4'-bipyridylium dichloride. These two-step reaction eventually results in prolonging the time for completion of the reaction and in the meantime the various adverse side reactions are brought about owing to the high reaction temperature. Furthermore methyl chloride will partially decompose into methanol and hydrochloric acid under high temperature in the presence of moisture (or water), and this acid further reacts with 4,4'-bipyridyl to form 4,4'-bipyridyl hydrochloric acid salt. These two undesirable side reactions will unavoidably occur, thus eventually bring down the yield of the product produced from the reaction of 4,4'-bipyridylium and methyl chloride. In the practical operation, the conversion of 4,4'-bipyridyl in quaternising reaction is around 90% in a preferable embodiment.

The same is true in case of using dimethyl sulphate as a quaternising agent. Dimethyl sulphate will partially decompose into methanol and sulfuric acid and the latter will react with 4,4'-bipyridyl to form the sulfuric acid salt of 4,4'-bipyridyl due to the water existing in the reaction solution and therefore resulting in the decrease of conversion. Moreover 1-methyl -4,(4'-pyridyl) pyridylium monomethyl sulphate will also be formed in the reaction, so that increase of total conversion to approximately 100% is impossible. In the practical operation the conversion is in the range of 93–94% in the most preferable instance. In accordance with the present invention, the reaction of 4,4'-bipyridyl with $X.R_1COOH$ is carried out in the intentional presence of water, namely in the presence of water which is sufficient to maintain the reaction phase in liquid state till the reaction end-point without formation of precipitate and which generally is 0.5–10 times of the amount of the 4,4'-bipyridyl used, to form acid salt in the first stage and this acid salt in the aqueous medium will generate $CO_2$ at high temperature due to separation of COOH and form the desired quaternised salt. This decomposition reaction in the second stage will proceed smoothly and reach approximately 100% when sufficient water exists in the reaction system, because in such system the generated $CO_2$ can be eliminated easily therefrom. These two reactions are effected successively within very short time therefore there is scarcely a chance for formation of impurities from the said side reaction. Accordingly, the reaction product can be placed directly into formulation without any purification.

The decisive factor for enhancing the conversion to as high as 99% or above is to terminate (complete) the reaction at a point when pH reaches an appropriate level. Theoretically speaking, when 1,1'-dialkyl -4,4'-bipyridylium dichloride has been formed and the reaction has been terminated, the pH value should fall in the range of neutrality. However, due to the chemical equilibrium, the intermediate i.e. 1-alkyl -4,(4'-pyridyl) pyridylium monochloride will inevitably remain in such neutral system. For the purpose of breaking the chemical equilibrium to thereby eliminate the said intermediate, an addition of a slight excess of $XR_1COOH$ may be necessary. From experiments, it has been found that the reaction is preferably completed at the point when pH reaches 2.0–3.0 and most preferably reaches 2.5. Completion of the reaction within the said pH range has shown that only less than 0.5% of the intermediate remained in the final product as analysed by the liquid chromatography.

The foregoing is the experiment conducted by employing monochloroacetic acid, and it is to be noted that similar results were obtained when employing the other α-halogen organic acids having the formular of $XR_1COOH$, wherein $R_1$ is a $C_1$-$C_3$ alkylene group and X is Br or Cl.

What we claim is:

1. A process for preparation of 1,1'-dialkyl-4,4'-bipyridylium dihalide which comprises reacting 4,4'-bipyridyl with an α-halogen substituted organic acid of the general formula: $XR_1COOH$, wherein X is Cl or Br in the α position, $R_1$ is a $C_1$-$C_3$ alkylene group, at a temperature from about 120° C. to 130° C. in the presence of water in an amount of from about 0.5–10 times that of the 4,4'-bipyridyl and positively controlling and terminating the reaction at a PH value of from about 2.0 to below 4.0.

2. A process in accordance with claim 1 wherein the reaction is completed when PH reaches from about 3.0 to 2.0.

3. A process in accordance with claim 2 wherein the α-halogen substituted organic acid is monochloroacetic acid.

* * * * *